United States Patent
Yan et al.

(10) Patent No.: US 10,092,644 B2
(45) Date of Patent: Oct. 9, 2018

(54) USE OF FLUORINATED CYCLIC DINUCLEOTIDES AS ORAL VACCINE ADJUVANTS

(71) Applicants: BROCK UNIVERSITY, St. Catharines, Ontario (CA); NATIONAL RESEARCH COUNCIL CANADA, Ottawa, Ontario (CA)

(72) Inventors: Hongbin Yan, St. Catharines (CA); Wangxue Chen, Nepean (CA); Rhonda Kuo Lee, Orleans (CA)

(73) Assignees: Brock University, St. Catharines (CA); National Research Council of Canada, Ottawa (CA)

(*) Notice: Subject to any disclaimer, the term of this patent is extended or adjusted under 35 U.S.C. 154(b) by 0 days.

(21) Appl. No.: 15/038,229

(22) PCT Filed: Nov. 18, 2014

(86) PCT No.: PCT/CA2014/051100
§ 371 (c)(1),
(2) Date: May 20, 2016

(87) PCT Pub. No.: WO2015/074145
PCT Pub. Date: May 28, 2015

(65) Prior Publication Data
US 2016/0287698 A1 Oct. 6, 2016

Related U.S. Application Data

(60) Provisional application No. 61/907,606, filed on Nov. 22, 2013.

(51) Int. Cl.
| | | |
|---|---|---|
| *A61K 39/39* | (2006.01) | |
| *A61K 31/7084* | (2006.01) | |
| *A61K 39/02* | (2006.01) | |
| *A61K 39/08* | (2006.01) | |
| *A61K 39/09* | (2006.01) | |
| *A61K 39/00* | (2006.01) | |

(52) U.S. Cl.
CPC .......... *A61K 39/39* (2013.01); *A61K 31/7084* (2013.01); *A61K 39/0208* (2013.01); *A61K 39/08* (2013.01); *A61K 39/092* (2013.01); *A61K 39/105* (2013.01); *A61K 2039/542* (2013.01); *A61K 2039/543* (2013.01); *A61K 2039/55561* (2013.01); *A61K 2039/57* (2013.01); *A61K 2039/6037* (2013.01)

(58) Field of Classification Search
None
See application file for complete search history.

(56) References Cited

U.S. PATENT DOCUMENTS

| | | |
|---|---|---|
| 7,569,555 B2 | 8/2009 | Karaolis |
| 7,592,326 B2 | 9/2009 | Karaolis |
| 2006/0040887 A1 | 2/2006 | Karaolis |
| 2008/0286296 A1 | 11/2008 | Ebensen et al. |
| 2013/0266612 A1 | 10/2013 | Fukasaka |

FOREIGN PATENT DOCUMENTS

WO   WO 2007/054279 A2   5/2007

OTHER PUBLICATIONS

MedlinePlus. Health Topics: Infections (2016) Web <https://medlineplus.gov/infections.html>.*
Shanahan, Carly. J. Am. Chem. Soc. (2011) 133, 15578-15592.*
International Search Report (PCT/ISA/210) dated Feb. 4, 2015, by the Canadian Patent Office as the International Searching Authority for International Application No. PCT/CA2014/051100.
Written Opinion (PCT/ISA/237) dated Feb. 4, 2015, by the Canadian Patent Office as the International Searching Authority for International Application No. PCT/CA2014/051100.
Ebensen et al., "The bacterial second messenger cyclic diGMP exhibits potent adjuvant properties", Vaccine, 2007, pp. 1464-1469, vol. 25.
Jenal, "Cyclic di-guanosine-monophosphate comes of age: a novel secondary messenger involved in modulating cell surface structures in bacteria?", Current Opinion in Microbiology, 2004, pp. 185-191, vol. 7.
Chen et al., "The potential of 3',5'-cyclic diguanylic acid (c-di-GMP) as an effective vaccine adjuvant", Vaccine, 2010, pp. 3080-3085, vol. 28.
Ogunniyi et al., "c-di-GMP is an effective immunomodulator and vaccine adjuvant against pneumococcal infection", Vaccine, 2008, pp. 4676-4685, 26(36).
Yan et al., "3',5'-Cyclic diguanylic acid elicits mucosal immunity against bacterial infection", Biochemical and Biophysical Research Communications, 2009, pp. 581-584, 387(3).
Libanova, R. et al., Cyclic Di-Nucleotides: New Era for Small Molecules as Adjuvants, Microbial Biotechnology, 2012, pp. 168-176, 5 (2), Society for Applied Microbiology and Blackwell Publishing.
Liu, P. et al., Fluorinated Nucleosides: Synthesis and Biological Implication, Journal of Fluorine Chemistry, 2008, pp. 743-766, 129, Elsevier B.V.
Zhou, J. et al., Potent Suppression of c-di-GMP Synthesis via I-site Allosteric Inhibition of Diguanylate cyclases with 2'-F-c-di-GMP, Bioorganic & Medicinal Chemistry, 2013, pp. 4396-4404, 21, Elsevier Ltd.
Extended European Search Report for EP 14863869.5 dated Apr. 7, 2017.

(Continued)

*Primary Examiner* — Deepak R Rao
*Assistant Examiner* — Laura M Daniel

(57) ABSTRACT

Disclosed is the use of fluorinated cyclic dinucleotides and pharmaceutically acceptable salts thereof as an adjuvant for the preparation of an oral vaccine. Further disclosed is the use of fluorinated cyclic dinucleotides and pharmaceutically acceptable salts thereof for enhancing the immune response to an orally administered vaccine.

10 Claims, 6 Drawing Sheets

(56) References Cited

OTHER PUBLICATIONS

Lee, Adrian et al., "A Standardized Mouse Model of Helicobacter pylori Infection: Introducing the Sydney Strain", Gastroenterology, vol. 112, pp. 1386-1397, 1997.
Tanha, Jamshid, et al., "Phage Display Technology for Identifying Specific Antigens on Brain Endothelial Cells", Methods in Molecular Medicine, vol. 89, The Blood-Brain Barrier: Biology Research Protocols, Humana Press Inc. pp. 435-449.
Chen, Wangxue, "Helicobacter Pylori Infection: Mechanism of Colonization and Functional Dyspepsia" "Reduced mlonization of gastric mucosa by Helicobacter pylori in mice deficient in interleukin-10" The Wakefield Gastroenterology Research Laboratory, Wakefield Hospital, Wellington, New Zealand, Journal of Gastroenterology and Hepatology (2001) 16, 377-383.
Yan, Hongbin, et al., "Synthesis of 3',5'-Cyclic Diguanylic Acid (cdiGMP) using 1-(4-Chlorophenyl)-4-Ethoxypiperidin-4-YL as a Protecting Group for 2'-Hydroxy Functions of Ribonucleosides" Nucleosides, Nucleotides, and Nucleic Acids, vol. 26, 189-204, 2007.
Zhang Jianbing, et al. "Pentamerization of Single-domain Antibodies from Phage Libraries: A Novel Strategy for the Rapid Generation of High-avidity Antibody Reagents", J. Mol. Biol., vol. 335, pp. 49-56. 2004.
Patel Girishchandra B., et al., "Mucosal and systemic immune responses by intranasal immunization using archaeal lipid-adjuvanted vaccines" ScienceDirect, Vaccine 25, pp. 8622-8636 2007.
Shu, et al., "Structure of STING bound to cyclic di-GMP reveals the mechanism of cyclic dinucleotide recognition by the immune system," Nat. Structure & Mol. Bio., 19(7): 722-725 (Jul. 2012).
Patel, et al. "Mucosal and systemic immune responses by intranasal immunization using archaeal lipid-adjuvanted vaccines," Vaccine 25 (2007) 8622-36.
Shi et al., "Helicobacter, Intranasal CpG-Oligodeoxynucleotide is a potent adjuvant of vaccine against Helicobacter pylori, and T Helper I type response and interferon-gamma correlate with the protection," (2005) 10(1) 71-79.
Kitagaki et al., "Oral administration of CpG-ODNs suppresses antigen-induced asthma in mice," Clin. and Exp. Immuno., (2005) 143: 249-259.

* cited by examiner

USE OF FLUORINATED CYCLIC DINUCLEOTIDES AS ORAL VACCINE ADJUVANTS

FIELD OF THE INVENTION

The present invention relates to the use of fluorinated cyclic nucleotides as adjuvants for oral vaccines, and in particular, oral vaccines for gastrointestinal infections.

BACKGROUND OF THE INVENTION

Vaccination as a prophylactic measure to prevent infectious diseases has proven to be extremely successful, leading to the eradication of a few and keeping many infectious diseases under control. Despite success in systemic vaccination, there has been an increasing unmet demand for effective mucosal vaccination.

The mucosal surfaces in humans (ca. 400 m² surface area) and animals are the major portals of entry and/or sites of diseases caused by bacterial, viral and parasitic pathogens. Examples of these diseases include those caused by enteropathogenic *E. coli, H. pylori, Campylobacter* spp., *Salmonella* spp, *Vibrio cholerae, Shigella* spp, rotaviruses, and calciviruses in the gastrointestinal (GI) tract; influenza virus, *Mycobacterium tuberculosis, Mycoplasma pneumoniae,* and respiratory syncytial virus in the respiratory tract; sexually transmitted diseases such as HIV, *Neisseria* spp., *Chlamydia* spp., and herpes simplex virus in the urogenital tract. However, the majority of currently licensed human and veterinary vaccines are administered parenterally and display only limited ability to elicit protective mucosal immunity. For example, systemic immunization with inactivated poliovirus can prevent development of poliomyelitis, but it fails to prevent infection in the GI tract or in the tonsils. Development of safe vaccines that elicit strong and prolonged mucosal immunity that would circumvent the attachment/colonization of pathogens to the mucosal epithelium, impede pathogen replication/penetration in the mucosa, and/or block activity of microbial toxins, would be a significant advancement in the prevention and treatment of a wide spectrum of infectious diseases. Mucosal vaccines would also improve patient compliance as well as alleviate safety and adverse reaction issues associated with injectable vaccines.

The mammalian mucosal immune system comprises innate, non-specific defenses and the adaptive immunologic network. Secretory IgA (S-IgA) is the best defined humoral effector component of the mucosal immune system, but its production is not sufficiently stimulated by current parenteral vaccines. The few mucosal vaccines currently on the market all use live-attenuated or dead whole cells. However, there are no mucosal vaccines using more defined protective antigens. Vaccines using subunit antigens are preferred from safety and regulatory perspectives. However, since most subunit antigens have poor immunogenicity and do not induce effective mucosal immunity on their own, potent mucosal adjuvants are required for the development of effective mucosal vaccines. Among the currently tested mucosal adjuvants, cholera toxin (CT) of *V. cholerae* and heat labile toxin (LT) of *E. coli* are the most effective. However, efforts to reduce the toxicity of these toxin adjuvants have generally also resulted in the loss or reduction of their mucosal adjuvanticity. The drawbacks of the current approaches to developing mucosal vaccines are fuelling intense global efforts to develop novel, safe vaccines/adjuvants that can induce protective mucosal immunity in vaccinated hosts.

As noted above, there are regulatory concerns with the use of poorly defined whole cell vaccines, as well as with live-attenuated vaccines, and with bacterial or viral vectors. The potential reversion to virulence of live-attenuated vaccines, potential dominant immune response to the live vector instead of the desired antigen with use of viral/bacterial vectors, and the contradiction of giving such vaccines to increasingly immunocompromised populations in the world are mitigating factors against the use/approval of similar new vaccines. Therefore, new mucosal vaccines must investigate other strategies. Research approaches for non-replicating mucosal delivery vehicles and adjuvants have included virosomes, liposomes, cochleates, archaeal lipid mucosal adjuvant vaccine and delivery system (AMVAD), polymeric microspheres, mucoadhesive polymers, immune stimulating complexes (ISCOMS), and CpG DNA as delivery/adjuvant systems, and the use of potent mucosal adjuvants such as cholera toxin (CT) and heat labile toxin (LT) from *E. coli*. However, CT and LT holotoxins have unacceptable adverse effects in humans, while their detoxified derivatives demonstrate diminished adjuvanticities. Although CpG shows some promise, there are still concerns regarding DNA integration, duration of immunity and the eliciting of unfavourable immune responses. As a result, no non-replicating, defined subunit mucosal vaccine has been approved to date. The poor immune responses of non-replicating antigen vaccines given mucosally are at least partially due to the lack of transport of the antigen through the epithelial layer to the mucosal immune network and the effective activation of antigen-presenting cells.

SUMMARY OF THE INVENTION

In one aspect, disclosed is a use of a fluorinated cyclic dinucleotide or a pharmaceutically acceptable salt thereof as an adjuvant for the preparation of an oral vaccine.

In a further aspect, disclosed is a method for preparing an oral vaccine, comprising admixing one or more non-replicating antigens with an adjuvant, wherein said adjuvant is a fluorinated cyclic dinucleotide In an embodiment of the disclosed use of a fluorinated cyclic dinucleotide as an adjuvant or the disclosed method for preparing an oral vaccine, the fluorinated cyclic dinucleotide has the following structure:

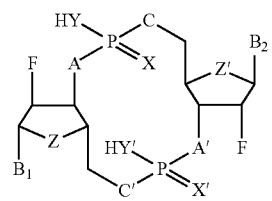

wherein A, C, A' and C' are independently selected from NH, O or S; X, Y, X', and Y' are independently selected from O or S; Z and Z' are independently selected from O, S, NH or $CH_2$; and $B_1$ and $B_2$ are independently a purine selected from:

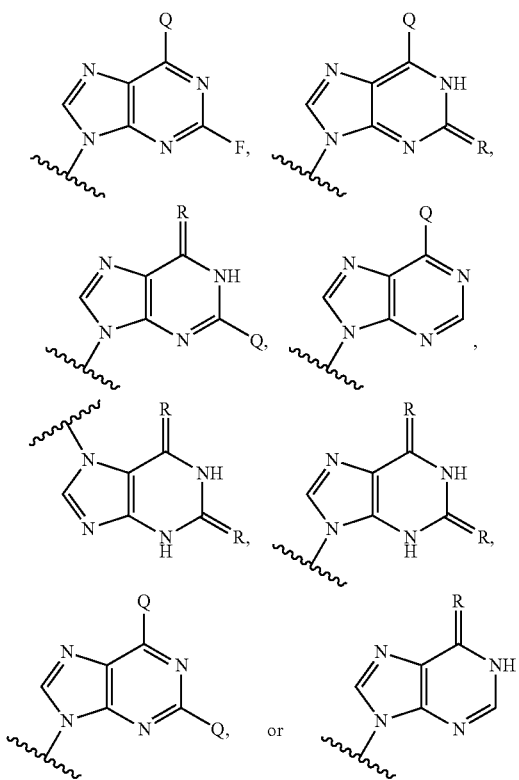

wherein Q is hydrogen or $NH_2$; nitrogen is optionally substituted with $C_1$-$C_6$ alkyl or $C_1$-$C_6$ acyl group; and R is O or S.

In a further embodiment of the disclosed use of a fluorinated cyclic dinucleotide as an adjuvant or the disclosed method for preparing an oral vaccine, the fluorinated cyclic dinucleotide is 2'-F-c-di-GMP having the following structure:

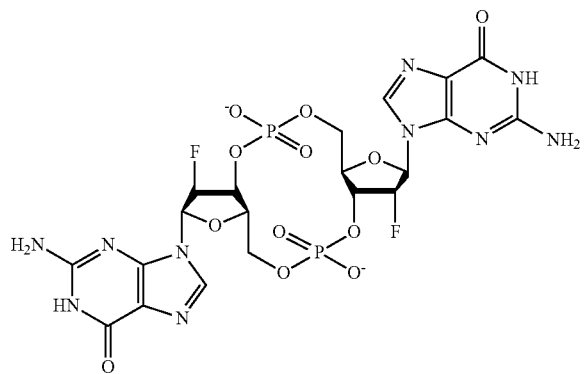

In a further embodiment of the disclosed use of a fluorinated cyclic dinucleotide as an adjuvant or the disclosed method for preparing an oral vaccine, the oral vaccine is an oral vaccine for the prevention or treatment of a bacterial infection comprising one or more non-replicating antigens.

In a further embodiment of the disclosed use of a fluorinated cyclic dinucleotide as an adjuvant or the disclosed method for preparing an oral vaccine, the bacterial infection is a gastrointestinal bacterial infection.

In a further embodiment of the disclosed use as an adjuvant or the disclosed method for preparing an oral vaccine, the gastrointestinal bacterial infection is a H. pylori infection, a C. difficile infection or a Listeria infection.

In a further aspect, provided is a method for enhancing an immune response to an orally administered vaccine comprising administering an oral vaccine with an effective amount of an adjuvant comprising a fluorinated cyclic dinucleotide or a pharmaceutically acceptable salt thereof.

In a still further aspect, disclosed is a use of an effective amount of a fluorinated cyclic dinucleotide or pharmaceutically acceptable salt of thereof for enhancement of an immune response to an orally administered vaccine.

In an embodiment of the disclosed method for enhancing an immune response or the disclosed use of a fluorinated cyclic dinucleotide for enhancement of an immune response, the fluorinated cyclic dinucleotide has the following structure:

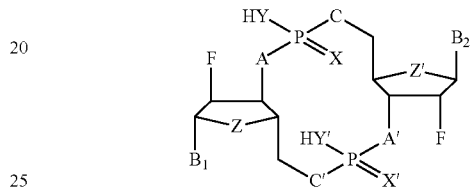

wherein A, C, A' and C' are independently selected from NH, O or S; X, Y, X', and Y' are independently selected from O or S; Z and Z' are independently selected from O, S, NH or $CH_2$; and $B_1$ and $B_2$ are independently a purine selected from:

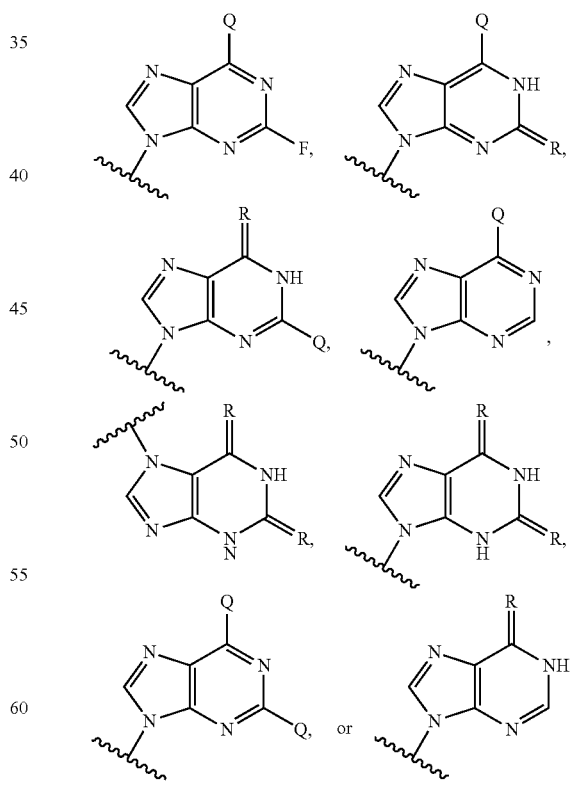

wherein Q is hydrogen or $NH_2$; nitrogen is optionally substituted with $C_1$-$C_6$ alkyl or $C_1$-$C_6$ acyl group; and R is O or S.

In a further embodiment of the disclosed method for enhancing an immune response or the disclosed use of a fluorinated cyclic dinucleotide for enhancement of an immune response, the fluorinated cyclic dinucleotide is 2'-F-c-di-GMP having the following structure:

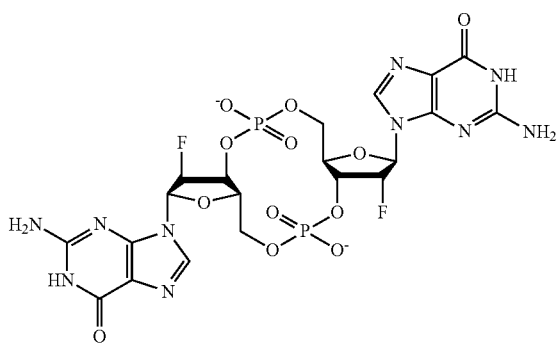

In a further embodiment of the disclosed method for enhancing an immune response or the disclosed use of a fluorinated cyclic dinucleotide for enhancement of an immune response, the oral vaccine is an oral vaccine for the prevention or treatment of an infection comprising one or more non-replicating antigens.

In a further embodiment of the disclosed method for enhancing an immune response or the disclosed use of a fluorinated cyclic dinucleotide for enhancement of an immune response, the infection is a gastrointestinal infection.

In a further embodiment of the disclosed method for enhancing an immune response or the disclosed use of a fluorinated cyclic dinucleotide for enhancement of an immune response, the gastrointestinal infection is a *H. pylori* infection, a *C. difficile* infection or a *Listeria* infection.

In a further embodiment of the disclosed method for enhancing an immune response or the disclosed use of a fluorinated cyclic dinucleotide for enhancement of an immune response, the vaccine and the adjuvant are administered as separate dosage forms.

In a further embodiment of the disclosed method for enhancing an immune response or the disclosed use of a fluorinated cyclic dinucleotide for enhancement of an immune response, the vaccine and the adjuvant are administered as an admixture.

In a further embodiment of the disclosed method for enhancing an immune response or the disclosed use of a fluorinated cyclic dinucleotide for enhancement of an immune response, the immune response comprises an antigen-specific mucosal immune response.

In a further embodiment of the disclosed method for enhancing an immune response or the disclosed use of a fluorinated cyclic dinucleotide for enhancement of an immune response, the immune response is characterized by an antigen-specific secretive IgA antibody response at mucosal sites.

In a further embodiment of the disclosed method for enhancing an immune response or the disclosed use of a fluorinated cyclic dinucleotide for enhancement of an immune response, the immune response further comprises an antigen-specific humoral immune response.

In a further embodiment of the disclosed method for enhancing an immune response or the disclosed use of a fluorinated cyclic dinucleotide for enhancement of an immune response, the immune response further comprises an antigen-specific cellular immune response.

In yet a further aspect, disclosed is an oral vaccine comprising a fluorinated cyclic dinucleotide or a pharmaceutically acceptable salt thereof and a composition comprising *H. pylori* antigen, wherein said fluorinated cyclic dinucleotide has the following structure:

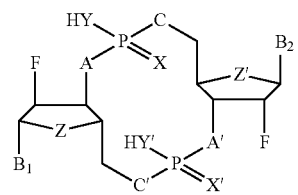

wherein A, C, A' and C' are independently selected from NH, O or S; X, Y, X', and Y' are independently selected from O or S; Z and Z' are independently selected from O, S, NH or $CH_2$; and $B_1$ and $B_2$ are independently a purine selected from:

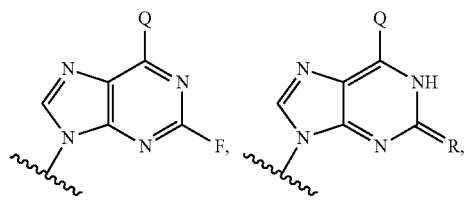

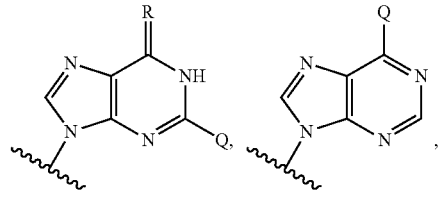

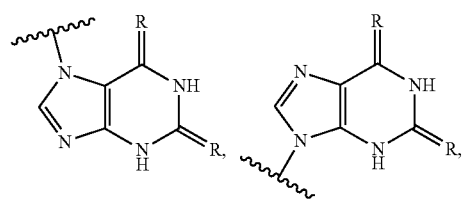

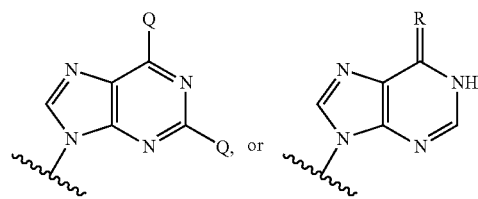

wherein Q is hydrogen or $NH_2$; nitrogen is optionally substituted with $C_1$-$C_6$ alkyl or $C_1$-$C_6$ acyl group; and R is O or S.

In an embodiment, the fluorinated cyclic dinucleotide is 2'-F-c-di-GMP having the following structure:

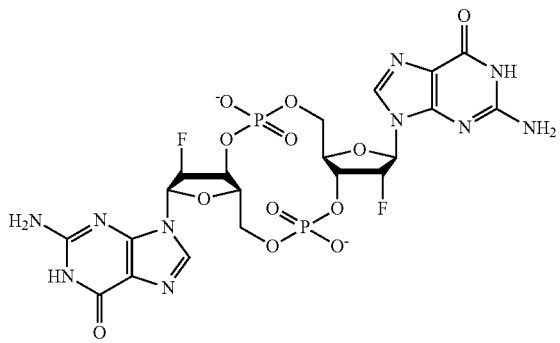

In a further embodiment, the composition comprising *H. pylori* antigen comprises *H. pylori* cell free extract or one or more *H. pylori* specific peptides and/or proteins.

DETAILED DESCRIPTION OF THE INVENTION

Figure 1:
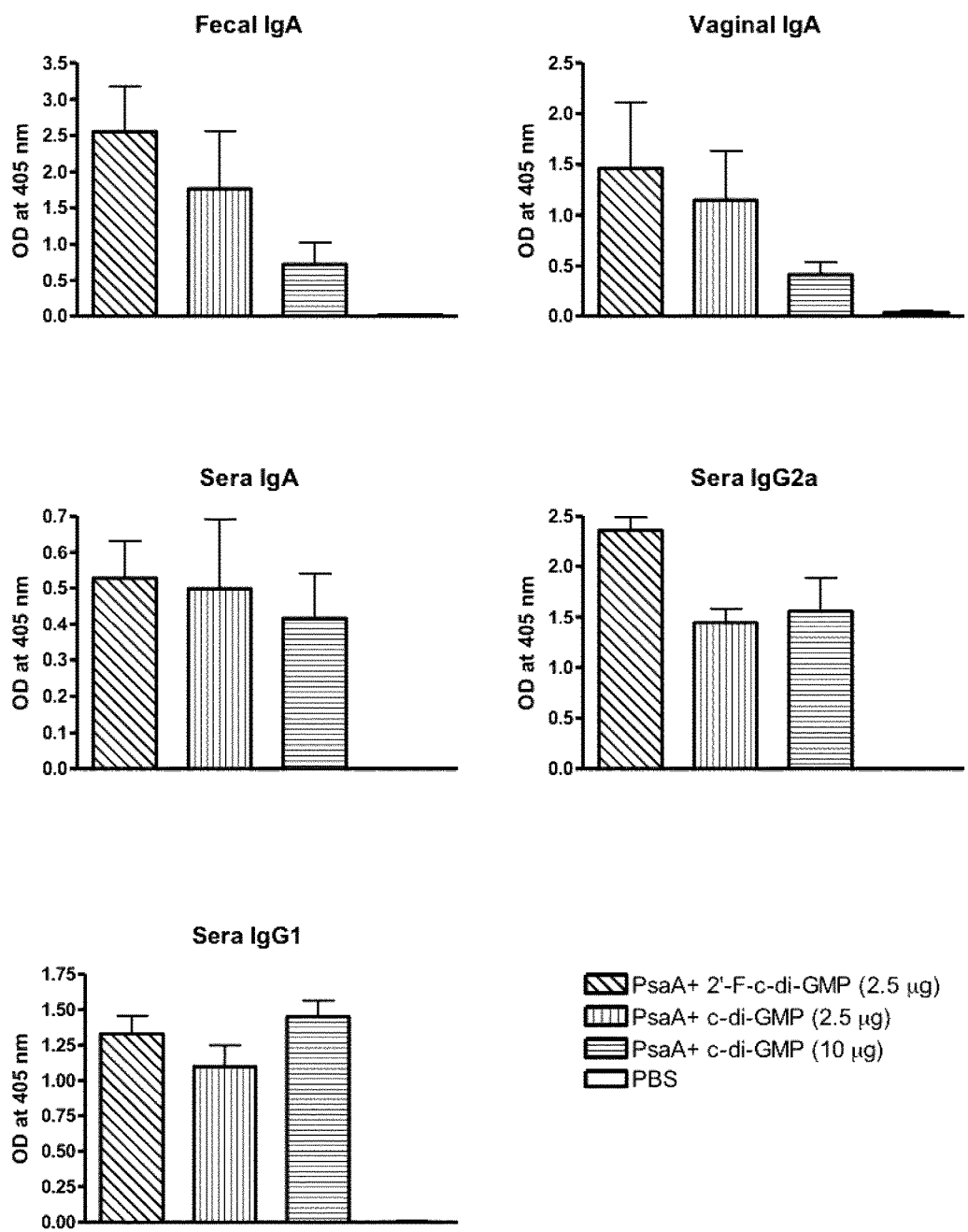
FIG. 1—bar graphs illustrating the effect of intranasal co-administration of PsaA+2'-F-c-di-GMP on PsaA-specific IgA levels in feces (top left panel), vaginal wash (top right panel), and serum (middle left panel) and additionally, IgG1 (bottom left panel) and IgG2a (middle right panel) levels in serum.

Cyclic di-guanosine monophosphate, or 3',5'-cyclic diguanylic acid, (c-di-GMP) has been shown to be a potent immunomodulator that stimulates cytokine and chemokines secretion and the maturation of dentritic cells (Chen et al. *The potential of 3',5'-cyclic diguanylic acid (c-di-GMP) as an effective vaccine adjuvant.* Vaccine, 28, 3080-3085, 2010). An enhanced antigen-specific antibody response has been observed in mice administered interperitoneally with *S. penuemoniae* pneumolysin toxid (PdB) or pneumococcal surface protection (PspA) adjuvanted with c-di-GMP (Chen et al, 2010; Ogunniyi et al. *c-di-GMP is an effective immunomodulator and vaccine adjuvant against pneumococcal infection.* Vaccine 26(36):4676-85, 2008). An enhanced antigen specific antibody response has also been observed in mice administered intranasally with pneumococcal surface adhesion A (Psa) together with c-di-GMP (Yan et al. 3',5'-*Cyclic diguanylic acid elicits mucosal immunity against bacterial infection.* Biochemical and Biophysical Research Communications, 2009, 387(3):581-4). While the use of c-di-GMP as a potential mucosal adjuvant has been suggested (Chen et al., 2010), previous studies have not investigated the use of cyclic dinucleotides as adjuvants for orally administered vaccines. U.S. Pat. Nos. 7,592,326 and 7,569,555 suggest that c-di-GMP and the c-di-GMP analogues disclosed therein can be used as an adjuvant to modulate any vaccine. However, there is no disclosure of an orally administered vaccine adjuvanted with c-di-GMP or any analogue thereof. At best, there is only the suggestion that c-di-GMP can be combined with a vaccine which is administered intranasally, intraperitoneally, subcutaneously, intramuscularly or intradermally for treatment of a *C. neoformans* infection or as part of an influenza vaccine administered intramuscularly. None of the examples in U.S. Pat. Nos. 7,592,326 and 7,569,555 demonstrate or suggest the use of c-di-GMP or any other cyclic dinucleotide as an adjuvant for an orally administered vaccine. US Patent Application No. 2008/0286296 suggests that the cyclic dinucleotides and conjugates disclosed therein can be used as mucosal adjuvants. However, there is no disclosure of an orally administered vaccine adjuvanted with the disclosed cyclic dinucleotides and conjugates. The examples in US Patent Application No. 2008/0286296 only demonstrate or suggest the use of the c-di-GMP and c-di-AMP as an adjuvant for a vaccine administered intranasally or intraperitoneally.

It is understood that orally administered vaccines as compared to intranasally, intraperitoneally, or other parenterally administered vaccines are subject to acid and enzymatic degradation in the gastrointenstinal (GI) tract and decreased availability due to first pass metabolism. In most cases, these vaccines are tolerated by the GI mucosal immune surfaces and thus do not lead to the induction of mucosal and systemic immune response. In addition, poor transport of antigens across the intestinal epithelium, antigen-microbiota interactions, and particle-mucous interactions in the GI lumen further impede the development of effective orally administered vaccines. Furthermore, mucosal adjuvants that are able to elicit immune response upon intranasal route of administration often fail to induce protective immunity when they are administered by oral route due to the compartmentalization of the mucosal immune system. Consequently, only a small fraction of mucosal adjuvants function when administered orally, although they work well when administered intranasally. As discussed above, currently available adjuvants and delivery systems for orally administered vaccines have unacceptable toxicities or poor adjuvanticity. The present disclosure is the first to describe the use of fluorinated cyclic dinucleotides, such as 2'-F-c-di-GMP, as adjuvants for orally administered vaccines for enhancing immunogenicity of orally administered vaccines.

As used herein, "antigen" means a compound or composition which, when introduced into an animal or a human in the appropriate context, will result in the formation of antibodies and/or cell-mediated immunity. "Non-replicating antigens" include but are not limited to modified inactivated infectious agents such as viruses and microorganisms (including bacteria, fungi, and yeast) or parts of such infection agents (including peptides, proteins, nucleic acids, oligosaccharides and polysaccharides).

As used herein, "adjuvant" means a compound or compounds that, when used in combination with appropriate antigens, augment, or otherwise alter or modify the resultant immune responses.

As used herein, "vaccine" means a composition comprising one or more antigens that is administered, typically with an adjuvant, to an animal or human to produce an antigen-specific immune response.

As used herein, "oral vaccine" means a vaccine which is orally administered to an animal or human.

As used herein, "enhanced immune response" means the increased magnitude or quantities of the reaction of the cells and fluids of the body to the presence of a substance that is not recognized as a constituent of the body itself. The immune response can be an humoral response, which involves the transformation of B cells into plasma cells that produce and secrete antibodies to a specific antigen, and/or a cell-mediated response produced when sensitized T cells directly attack foreign antigens and secrete lymphokines that initiate the body's humoral immune response.

Disclosed herein is the use of a fluorinated cyclic dinucleotide according to Formula (I):

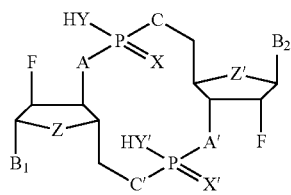

wherein A, C, A' and C' are independently selected from NH, O or S; X, Y, X', and Y' are independently selected from O or S; Z and Z' are independently selected from O, S, NH or $CH_2$; and $B_1$ and $B_2$ are independently a purine selected from:

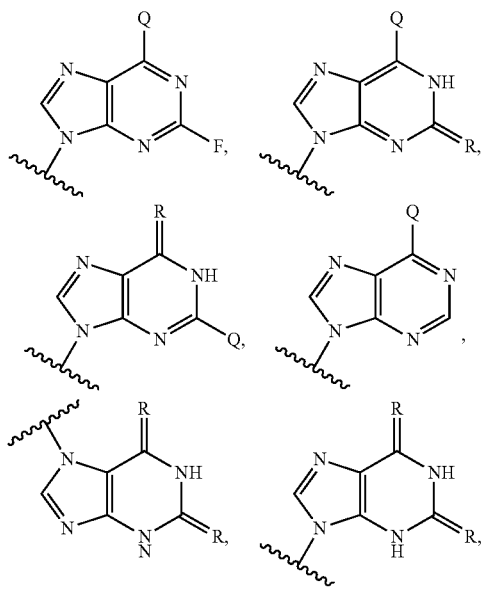

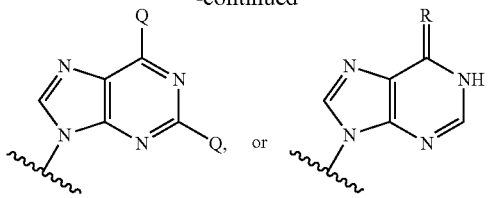

wherein Q is hydrogen or $NH_2$; nitrogen is optionally substituted with $C_1$-$C_6$ alkyl or $C_1$-$C_6$ acyl group; and R is O or S, or a pharmaceutically acceptable salt thereof, as an adjuvant for the preparation of an oral vaccine or for the enhancement of an immune response in response to an orally administered vaccine.

In an embodiment, the fluorinated cyclic dinucleotide according to Formula (I) is 2'-F-c-di-GMP having the following structure.

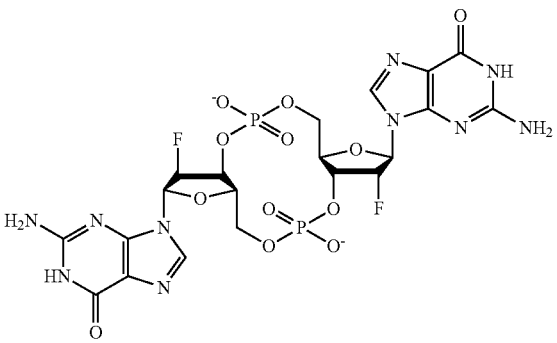

The fluorinated cyclic dinucleotide according to Formula (I) can be formulated as neutral or salt forms. Pharmaceutically acceptable salts include those formed with cations such as those derived from but not limited to sodium, potassium, ammonium, calcium, ferric hydroxides, isopropylamine, triethylamine, 2-ethylamino ethanol, histidine, or procaine.

The fluorinated cyclic dinucleotide according to Formula (I) is expected to have good stability in the gastrointestinal tract and particularly, resistance to acid degradation in stomach fluids. Without being bound to any particular theory, it is believed that resistance to degradation in the gastrointestinal tract enhances the efficacy of the fluorinated cyclic dinucleotide according to Formula (I) to act as an oral adjuvant and to enhance the immune response to oral vaccines. A further benefit of the fluorinated cyclic dinucleotide according to Formula (I) is that it can be easily synthesized in comparison to many other cyclic dinucleotides. For example, 2'-F-c-di-GMP is easier to synthesize as compared with c-di-GMP as the synthesis of 2'-F-c-di-GMP does not require protection on the 2'-OH as is the case for c-di-GMP.

The fluorinated cyclic dinucleotide according to Formula (I) or a pharmaceutically acceptable salt of thereof, can be used as an adjuvant for the preparation of an oral vaccine. The oral vaccine is preferably a vaccine which produces an antigen-specific immune response at local (site of immunization) and distal mucosal tissues (such as the respiratory and urogenital systems) as well as in the systemic tissues (such as blood, etc.) when administered orally. In one embodiment, the oral vaccine is for the prevention or treatment of an infection caused by bacteria, viruses, parasites, protozoa, or fungus. In a further embodiment, the oral vaccine is for the prevention or treatment of a gastrointestinal infection. Examples of gastrointestinal infections include infections caused by *H. pylori, E. coli, C. jejuni, S. typhimurium*, rotavirus, norovirus, *C. difficile* and *Listeria*. Such oral vaccines can comprise one or more non-replicating antigens. The one or more non-replicating antigens may include native, modified, or inactivated whole cells, and cell components, including peptides, proteins, nucleic acids, oligosaccharides and polysaccharides.

In one embodiment, the oral vaccine is an oral vaccine for the prevention or treatment of a *H. pylori* infection and a fluorinated cyclic dinucleotide according to Formula (I) or a pharmaceutically acceptable salt is used as an adjuvant. In a preferred embodiment the fluorinated cyclic dinucleotide according to Formula (I) is 2'-F-c-di-GMP. The oral vaccine can comprise *H. pylori* cell free extracts or one or more *H. pylori* specific peptides and/or proteins.

Disclosed is a method for preparing an oral vaccine comprising admixing one or more non-replicating antigens with an adjuvant comprising the fluorinated cyclic dinucleotide according to Formula (I) and more preferably, 2'-F-c-di-GMP. The oral vaccine can be prepared as a single oral dosage form wherein the fluorinated cyclic dinucleotide according to Formula (I) or pharmaceutically acceptable salt thereof are admixed with the one or more non-replicating antigens.

The relative effective amounts of the components comprising the oral vaccine, including the one or more non-replicating antigens and the fluorinated cyclic dinucleotide or pharmaceutically acceptable salt thereof, can be determined using methods known in the art. Typically, this involves testing vaccine formulations in animals starting with a low dose of the formulation and then increasing the dosage while monitoring the specific immune response and the protection against infection.

For embodiments wherein the oral vaccine is an oral vaccine for the prevention or treatment of *H. pylori* infection and a fluorinated cyclic dinucleotide according to Formula (I), preferably 2'-F-c-di-GMP, or a pharmaceutically acceptable thereof, is used as an adjuvant, the weight ratio of *H. pylori* cell free extract (HPCE) to the fluorinated cyclic dinucleotide according to Formula (I) or pharmaceutically acceptable salt thereof can be from about 1 to 50, more preferably about 1 to 10, and even more preferably about 1 to 5.

In addition to the antigen and adjuvant compounds, the oral vaccine may comprise suitable carriers, excipients and auxiliaries which facilitate the preparation of dosage forms for oral administration, including solutions or other liquid forms, tablets, capsules, and granules. The oral dosage forms may be provided with a suitable enteric coating, if desired.

The oral dosage forms may include excipients including fillers, binders, and disintegrating agents. Examples of fillers include sugars (e.g. lactose or sucrose mannitol or sorbitol), cellulose preparations, and/or calcium phosphates (e.g. tricalcium phosphate or calcium hydrogen phosphate). Examples of binders include starches (e.g. maize starch, wheat starch, rice starch, or potato starch), gelatin, gum tragacanth, methyl cellulose, hydroxypropylmethylcellulose, sodium carboxymethylcellulose, and/or polyvinyl pyrrolidone. Examples of disintegrating agents include starches discussed above, as well as carboxymethyl starch, cross-linked polyvinyl pyrrolidone, agar, or alginic acid or a salt thereof. The oral dosage forms may further include auxiliaries including flow-regulating agents and lubricants, such as silica, talc, stearic acid or salts thereof (e.g magnesium stearate or calcium stearate) and/or polyethylene glycol.

The oral vaccines disclosed herein can be manufactured by methods known in the art including but not limited to mixing, granulating, dissolving, lyophilizing processes. It will be understood that the choice of manufacturing process will depend on the physical properties of the vaccine ingredients used.

Many bacterial (for example, *Campylobacter* and *E. coli*) and viral (for example, rotavirus and norovirus) pathogens are extracellular organisms or have a significant extracellular life for their colonization, replication, and dissemination. It is well known and demonstrated in the published literature that antigen-specific IgA at mucosal sites and IgG in the blood are protective against the infections caused by these pathogens. It has now been determined that the fluorinated cyclic dinucleotide according to Formula (I) can be used to enhance the immune response elicited by oral vaccines for such pathogens.

In another aspect, provided is a method for enhancing an immune response to an orally administered vaccine, comprising: administering an oral vaccine with an effective amount of an adjuvant comprising of a fluorinated cyclic dinucleotide according to Formula (I) or a pharmaceutically acceptable salt thereof.

In an embodiment, the fluorinated cyclic dinucleotide is 2'-F-c-di-GMP having the structure shown below.

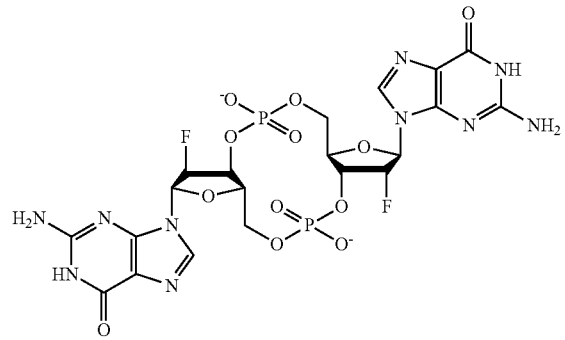

The fluorinated cyclic dinucleotide according to Formula (I) or pharmaceutically acceptable salt thereof can be used to enhance the immune response to an oral vaccine which preferably produces an antigen-specific mucosal immune response when administered. In one embodiment, the oral vaccine is for the prevention or treatment of an infection caused by bacteria, viruses, parasites/protozoa, and fungus. In a further embodiment, the oral vaccine is for the prevention or treatment of an infection. Examples of gastrointestinal infections include infections caused by *H. pylori, E. coli, C. jejuni, S. typhimurium*, rotavirus, norovirus, *C. difficile* and *Listeria*. Such oral vaccines can comprise one or more non-replicating antigens. The one or more non-replicating antigens may include inactivated whole cells, and cell components, including peptides, proteins, nucleic acids, oligosaccharides and polysaccharides.

In one embodiment, the oral vaccine is an oral vaccine for the prevention or treatment of a *H. pylori* infection and a fluorinated cyclic dinucleotide according to Formula (I), preferably 2'-F-c-di-GMP, or a pharmaceutically acceptable salt thereof is used as an adjuvant. The oral vaccine can comprise *H. pylori* extracts cell free extracts or one or more *H. pylori* specific peptides or proteins.

Administration of the oral vaccine with an effective amount of an adjuvant comprising a fluorinated cyclic dinucleotide according to Formula (I) or a pharmaceutically acceptable salt thereof enhances the immune response elicited by the oral vaccine alone. Enhancement of the immune response may include an antigen-specific mucosal immune response which would otherwise be absent or elicited to a lesser degree when an equal dosage of a selected oral vaccine is administered to a host without the adjuvant (for example, as evidenced by lowered antibodies titres, cell proliferation or secretion of certain cytokines or toxic substances, or expression of activation markers in the surface of immune cells). The enhanced mucosal immune response may be characterized by an antigen-specific secretive IgA antibody response at mucosal sites. The enhanced immune response may further comprise an antigen-specific humoral immune response and/or an antigen-specific cellular immune response either of which would otherwise be absent or elicited to a lesser degree when an equal dosage of the selected oral vaccine is administered to a patient without the adjuvant.

It will be understood that the type of immune response and the degree of enhanced immunogenicity will depend on the type and amount of oral vaccine administered and the recipient. The relative effective amounts of the oral vaccine and adjuvant can be determined using conventional methods as described above.

For embodiments wherein the oral vaccine is an oral vaccine for the prevention or treatment of *H. pylori* infection and a fluorinated cyclic dinucleotide according to Formula (I), preferably 2'-F-c-di-GMP, or a pharmaceutically acceptable thereof is used as an adjuvant, the weight ratio of *H. pylori* cell free extract (HPCE) to the fluorinated cyclic dinucleotide according to Formula (I) or pharmaceutically acceptable salt thereof can be from about 1 to 50, more preferably about 1 to 10, and even more preferably about 1 to 5.

In one embodiment, the vaccine and the adjuvant can be orally administered as separate dosage forms.

In another embodiment, the vaccine and the adjuvant can be orally administered as an admixture in a unitary dosage form, including as any of the oral dosage forms described above.

While this invention has been described in connection with specific embodiments and chemical structures, it will be apparent to those skilled in the art that variations and modifications may be made without departing from the invention. The invention includes all such variations and modifications as fall within the scope of the appended claims. The following examples further illustrate the invention and are not intended to limit the invention in any manner.

EXAMPLES

Materials and Methods c-di-GMP. c-di-GMP was synthesized according to procedures reported previously. (Yan, H.; Anguilar, A. L. *Synthesis of 3',5'-cyclic diguanylic acid (c-di-GMP)*, Nucleoside, Nucleotides & Nucleic Acids. 2007, 26, 189.)

2'-F-c-di-GMP. 2'-F-c-di-GMP was synthesized according to procedures reported previously (Yan, H.; Anguilar, A. L. *Synthesis of 3',5'-cyclic diguanylic acid (c-di-GMP)*, Nucleoside, Nucleotides & Nucleic Acids. 2007, 26, 189).

Cholera toxin (CT). CT was purchased from Sigma-Aldrich Canada Ltd. (Oakville, Ontario, Canada).

Production of recombinant pneumococcal surface adhesion A (PsaA) of *S. pneumonia*. The PsaA gene from type 14 isolate of *S. pneumoniae* was amplified by colony PCR using the primer set PsaA-BspM-F (GAAGAAACCTGCA-CAACAACAGGCCGCTAGCG-GAAAAAAAGATRCARCTTC) and PsaAH-Hind-R (TAATAAAAGCTTTCACTAATGGTGATGGTGATG-GTGGGATCCACCGCCTCCTTTTGCCAATCCTTCAG-CAATC). The reaction also in-frame fused DNA encoding 6× His tag to the 3'-end of the PsaA gene. The PCR product was digested with BspMI and HindIII and ligated into a periplasmic expression vector pSJF2 (Tanha J, Muruganandam A, Stanimirovic D (2003). *Phage display technology for identifying specific antigens on brain endothelial cells*. Methods Mol. Med. 89: 435-449.), which was further digested with the same enzymes to generate a clone expressing PsaAH. The PsaAH clone was then purified with immobilized metal affinity chromatography (IMAC) as previously described (Zhang J, Tanha J, Hirama T, Khieu N H, To R, et al. (2004). *Pentamerization of single-domain antibodies from phage libraries: a novel strategy for the rapid generation of high-avidity antibody reagents*. J. Mol. Biol. 335: 49-56.). The recombinant *Escherichia coli* culture harboring the plasmid encoding for PsaAH was cultivated at 28° C. in 24 L of Luria broth supplemented with 0.2 mg/ml penicillin, in a fermenter vessel. The starting culture optical density ($OD_{600}$) was 0.17, and the pH was maintained at 7.2 and the dissolved oxygen at 20% saturation during cultivation. Once an $OD_{660}$ of 0.50 was achieved, 2 g isopropyl-beta-D-thiogalactopyranoside (IPTG) was added to induce the culture. At 21 h post-induction, the culture had reached an $OD_{600}$ of 3.90, and approximately 180 g wet wt of cells were collected upon harvesting by a combination of ultrafiltration and centrifugation. The cells were frozen at −20° C. until used for PsaA extraction. Cell pellets were lysed with an Emulsiflex Cell Disruptor (Avestin Inc. Ottawa, ON). Following centrifugation of the cell lysate, the clear supernatant was loaded onto a Hi-Trap™ Chelating affinity column (Amersham Biosciences) and the 6× His-tagged proteins were purified following the manufacturer's instructions. A total of 47 mg of PsaA protein was obtained.

Preparation of *H. pylori* cell-free sonicate extract (HPCE). *H. pylori* SS1 were grown on Columbia agar supplemented with 10% Laked horse blood for 48-72 h at 37° C. under microanaerobic conditions generated with CampyGen™ in an AnaeroJar™ (Oxoid, Hampshire, UK). The bacterial cells were harvested by centrifugation at 12 000 g for 10 min at 4° C., washed with phosphate-buffered saline (PBS) three times and then suspended in 15 mL PBS. The cells were disrupted by sonication with a Branson sonifier (model B15, Branson Sonic Power Company, Banbury, Conn., USA) at 30 s intervals (60% pulses) for 5 min on ice. The cell debris and unbroken cells were removed by centrifugation at 14,000 g for 20 min at 4° C. The supernatant was aliquoted and stored at −80° C. until use. Protein concentrations of the extract were determined by the Bradford method (Bio-Rad Laboratories, Hercules, Calif., USA) and by using bovine serum albumin as the standard.

Mice. Six to eight-week-old female BALB/c or C57BL/6 mice were purchased from Charles Rivers Laboratories (St. Constant, Quebec). The animals were housed under specific-pathogen-free conditions in a federally licensed small animal containment level 2 facility, and given free access to sterile water and certified mouse chow. The animals were maintained and used in accordance with the recommendations of the Canadian Council on Animal Care Guide to the Care and Use of Experimental Animals, and the experimental procedures were approved by the institutional animal care committee.

Intranasal or oral immunization in mice. For intranasal immunization, mice were lightly anesthetized under isofluorane. On day 0, 14 and 21, groups of mice (n=5) were inoculated with 50 µl of various vaccine preparations or controls as detailed in Examples 1-5. For oral immunization, various vaccine preparations or controls in 0.2 ml volume were administered by gavage via an 18-gauge feeding needle.

At day 28, blood and mucosal samples (fecal pellets or/and vaginal wash) were collected as described elsewhere (Patel G B, Zhou H, Ponce A, Chen W (2007). *Mucosal and systemic immune responses by intranasal immunization using archaeal lipid-adjuvanted vaccines*. Vaccine 25: 8622-8636.). In some experiments, nasal wash samples were also collected at the end of experiment. For both the vaginal and nasal wash, the volume of the lavage fluid recovered from each mouse was recorded. Since the recovery of lavage volumes among different mice in our study were very similar (about 90%), the small variation among individual samples was not adjusted. All samples were stored at −20° C. until assay.

Vaginal wash samples were collected by slowly injecting and withdrawing (3-4 times) 50 µl PBS (pH 7.2) into the vagina of conscious mice, using a P100 pipette. The volume of the vaginal lavage fluid recovered from each mouse was recorded.

Enzyme-linked immunosorbent assay (ELISA) for PsaA-specific IgA and IgG isotypes. Levels of PsaA-specific antibodies in serum and mucosal samples were measured by an enzyme-linked immunosorbent assay (ELISA) modified from a previously described procedure (Yan H, Kuo Lee R, Tram K, Qiu H, Zhang J, Patel G B, Chen W. *3',5'-Cyclic diguanylic acid elicits mucosal immunity against bacterial infection*. Biochemical and Biophysical Research Communications, 2009; 387(3):581-4.). Briefly, 96-well Immunolon $2^R$ microplates (Thermo Electron Corporation, Milford, Mass.) were coated with 0.5 µg PsaA/well in 100 µl of 0.015 M sodium carbonate and 0.035 M sodium bicarbonate buffer (pH 9.6) at 4° C. overnight. All the subsequent incubations were carried out at room temperature. The wells were blocked by incubation with 5% bovine serum in PBS for 1 h, and then rinsed three times with PBS-0.05% Tween 20. Duplicates of 100 µl pre-diluted samples were added to the wells. Sample dilutions were as follows: 1:2 for fecal extracts and nasal washes, 1:2000 for serum IgG1, 1:500 for serum IgG2a and 1:50 for serum IgA. After the plates were incubated for 3 h, alkaline phosphatase-conjugated goat antibodies specific for mouse IgA, IgG1 and IgG2a (all from Caltag Laboratories, Burlingame, Calif.) were added and incubated for 1 h. Color reactions were developed by the addition of p-nitrophenyl phosphate (pNPP) substrate (KPL, Inc., Gaithersburg, Md.), and optical density was measured at 405 nm with an automated ELISA plate reader (Multiskan Ascent, Thermo Labsystems, Vantaa, Finland). Pooled samples collected from mice that had been intranasally immunized with the PsaA+CT or from the naïve mice were used as positive or negative controls respectively.

Measurement of *H. pylori*-specific antibodies in the serum and mucosal samples. Antibodies specific for *H. pylori* were measured by an enzyme-linked immunosorbent assay (ELISA) modified from a previously described procedure (Chen W, Shu D, Chadwick V S. *Reduced colonization of gastric mucosa by Helicobacter pylori in mice deficient in interleukin*-10. J. Gastroenterol. Hepatol. 2001 April; 16(4): 377-83.). Briefly, 96-well Immunolon 4 plates (Dynex Technologies Inc., Chantilly, Va., USA) were coated with sonicated whole-cell extracts of *H. pylori* SS1 (20 µg/mL; 50 µL/well) in carbonate-bicarbonate buffer (pH 9.5) at 4° C. overnight. The plates were blocked by an incubation with 1% gelatin in phosphate-buffered saline at room temperature for 1 h, and then rinsed four times with PBS with 0.05% Tween 20. Prediluted 100 µL serum samples (1:50) were added to the wells, and the plates were incubated at room temperature for 3 h. Thereafter, alkaline phosphatase-conjugated goat antibodies specific for mouse IgA, and IgG (Sigma Chemical Co., St Louis, Mo., USA), and horseradish peroxidase-conjugated rabbit antibodies specific for mouse IgG1, IgG2a, IgG2b, IgG3 and IgM (all from Serotec Ltd, Oxford, UK) were added for 2 h at room temperature. Color reactions were developed by the addition of p-nitrophenyl phosphate (pNPP) or 2,2'-azinobis(3-ethylbenzthiazoline-sulfonic acid) (Sigma) substrates, and optical density was measured at 405 nm with an automated ELISA plate reader (Anthos 2001; Anthos Labtec, Salzburg, Austria). Controls for the assay included serum samples from mice orally immunized with *H. pylori* antigens with cholera toxin as an adjuvant, and serum samples from naive mice, respectively.

Intranasal challenge of mice with *S. pneumoniae*. Fresh inocula were prepared for each experiment from a frozen stock of *S. pneumoniae* (type 14). Stock vials of *S. pneumoniae* were thawed and the culture revived on chocolate agar, which was then used to inoculate Todd-Hewitt and Columbia broth supplemented with 1% glucose and 0.1% sodium bicarbonate. The broth culture was incubated in a candle jar at 37° C. for approximately 6 h. The broth culture in mid-logarithmic growth phase was centrifuged at 12,000×g for 15 min, cells were resuspended in PBS and used immediately. Fourteen days after the last immunization, mice were anesthetized and intranasally inoculated with approximately $10^7$ colony-forming units (CFU) *S. pneumoniae* in 50 µl saline. The actual inoculum concentrations were determined by plating 10-fold serial dilutions on chocolate agar. Inoculated mice were sacrificed 3 days later and the nasal cavity was lavaged with 0.5 ml lavage fluid and aliquots (100 µl) of 10-fold serial dilutions of the lavage fluids were cultured, in duplicates, on chocolate agar plates to quantify the number of viable organisms.

*H. pylori* and oral *H. pylori* infection. The mouse-adapted *H. pylori* SS1 that was established by Lee et al. (Lee A, O'Rourke J, De Ungria M C, Robertson B, Daskalopoulos G, Dixon M F. *A standardized mouse model of Helicobacter pylori infection*. Gastroenterology 1997; 112: 1386-97.) was used for all experiments. Bacteria were grown on brain-heart infusion (BHI) broth supplemented with 5% horse serum under a microaerophilic atmosphere created by a CampyGen generator (Oxoid Ltd, Hampshire, England) at 37° C. for 48 h. The organisms were positively identified on the basis of morphology and presence of urease enzyme activity, and via PCR amplification of the cagA gene by using specific primers.

The mice were inoculated orally with $1\times10^8$ colony-forming units (CFU) of freshly harvested *H. pylori* in 500 µL BHI broth by using a 19-gauge feeding needle as described previously. The inoculations were repeated twice (a total of three inoculations) over a period of 5 days. Mice were killed by an overdose of carbon dioxide 4-6 weeks after the last inoculation, and the serum and stomachs of the animals were collected for analysis.

Assessment of *H. pylori* infection. The presence of *H. pylori* infection in individual mice was determined by quantitative bacterial culture as described previously (Chen W, Shu D, Chadwick V S. *Reduced colonization of gastric mucosa by Helicobacter pylori in mice deficient in interleukin*-10. J. Gastroenterol. Hepatol. 2001 April; 16(4):377-83.). Briefly, the mouse stomach was opened longitudinally along the greater curvature and gently washed three times in PBS to remove the stomach contents. The stomach tissue was then homogenized in 5 ml saline with Teflon pestles and glass tubes. The homogenates were serially diluted in saline, and 100 µl of the dilutions were plated onto GSS (Glaxo Selective Supplement Antibiotics)-supplemented agar plates. The plates were incubated for 96 h at 37° C. under microaerophilic conditions, and the number of colonies were counted and expressed as CFU/stomach. With this method, $\log_{10}$ 2.7 CFU/stomach represented the limit of detection. The data were analyzed using the Mann-Whitney test, using GraphPad software version 5.0.

Preparation of flagellins from *L. monocytogenes* and *C. difficile*. Bacterial strains were grown overnight at 37° C. on agar plates. Cells were scraped from surface and resuspended in 10 mM Tris pH7.4. Flagella were sheared from surface of bacterial cells using a warring blender (4×1 min). Bacterial cells were removed by low speed centrifugation and then flagellar filaments were collected from supernatant by ultracentrifugation (100,000×g, 1 hour). Flagellar samples were analysed by SDS-PAGE.

Measurement of flagellin-specific antibodies in the serum and mucosal samples. Antibodies specific for *L. monocytogenes* flagellin and *C. difficile* flagellin were measured by an enzyme-linked immunosorbent assay (ELISA) modified from a previously described procedure (Chen W, Shu D, Chadwick V S. *Reduced colonization of gastric mucosa by Helicobacter pylori in mice deficient in interleukin*-10. J. Gastroenterol. Hepatol. 2001 April; 16(4):377-83.). Briefly, 96-well Nunc Immunoplate II plates (VWR) were coated with purified flagellins (5 µg/mL; 50 µL/well) in carbonate-bicarbonate buffer (pH 9.5) at 4° C. overnight. The plates were blocked by an incubation with 1% bovine serum albumin in phosphate-buffered saline with 0.1% $NaN_3$ at room temperature for 1 h, and then rinsed three times with PBS with 0.05% Tween 20. Prediluted 100 µL serum samples (1:100) or fecal extracts (1:2 dilution) were added to the wells, and the plates were incubated at room temperature for 3 h. Thereafter, alkaline phosphatase-conjugated rabbit antibodies specific for mouse IgA, IgG1, and IgG2a (all from Serotec Ltd, Oxford, UK) were added for 1 h at room temperature. Color reactions were developed by the addition of p-nitrophenyl phosphate (pNPP)(Sigma) substrates, and optical density was measured at 405 nm with an automated ELISA plate reader (Anthos 2001; Anthos Labtec, Salzburg, Austria).

Statistical analysis. Data are presented as mean±SD for parametric data, and median with ranges for non-parametric data. Differences in the number of bacteria between groups of animals were determined by using the Student's t-test. Differences in the severity of gastritis and antibody titers were determined by using the Mann-Whitney U-test. Differences were considered significant for a P value of ≤0.05.

Example 1

Intranasally Administered 2'-F-c-di-GMP Induces Strong Antigen-specific Antibody Responses in the Serum and at Multiple Mucosal Sites To determine if 2'-F-c-di-GMP can elicit mucosal immune responses to microbial (bacterial and viral) antigens, groups of BALB/c mice were intranasally (i.n.) immunized with 2 µg recombinant PsaA protein of *S. pneumoniae* admixed with 2.5 µg 2'-F-c-di-GMP, 2.5 µg c-di-GMP, or 10 µg c-di-GMP at day 0, 14 and 21. An additional group of mice was sham-immunized with PBS only. The blood and mucosal samples (fecal pellets and vaginal wash) were collected at day 28 and assayed for PsaA-specific IgA, IgG1 and IgG2a by standard ELISA. As seen in FIG. 1, co-administration of PsaA with 2'-F-c-di-GMP induced high level of PsaA-specific IgA in feces, nasal wash, and serum as well as serum IgG1 and IgG2a levels. As expected, sham-immunized mice showed no specific antibody responses in the serum or mucosal samples as shown in FIG. 1. The results showed that, compared to parental c-di-GMP, 2'-F-c-di-GMP induces stronger antigen-specific IgA responses in feces and vaginal washings and IgG2a responses in the serum. These results indicate that 2'-F-c-di-GMP is a potent mucosal adjuvant when administered by intranasal route. These results demonstrate that 2'-F-c-di-GMP can enhance mucosal immune responses to microbial antigens and can be further developed as a potential mucosal adjuvant.

Example 2

Intranasal Immunization of Mice with 2'-F-c-di-GMP-adjuvanted PsaA Reduces Nasopharyngeal Colonization by *S. Pneumoniae*

Figure 2:
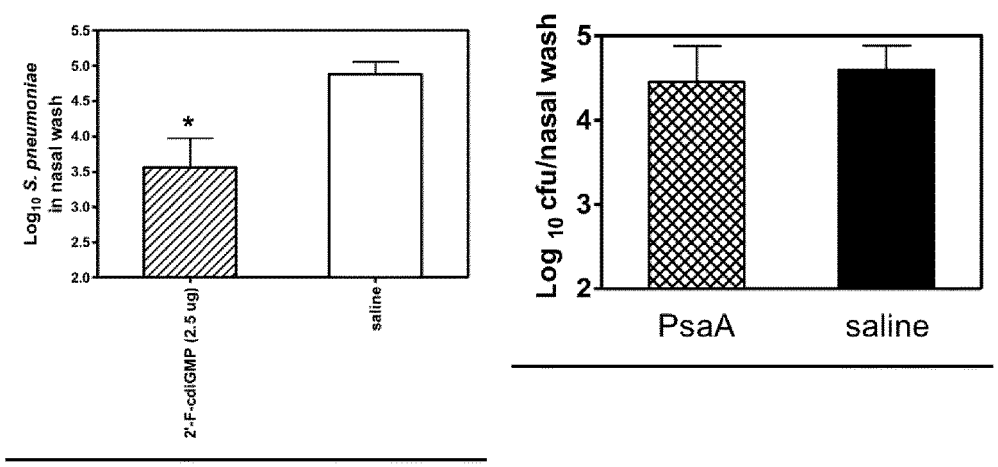
FIG. 2—bar graphs comparing *S. pneumoniae* colonization in mice intranasally immunized with PsaA 30 2'-F-c-di-GMP (left panel) or in sham-immunized (saline) mice (right panel).

Next, it was determined if the mucosal immune responses induced by the 2'-F-c-di-GMP adjuvanted vaccine are protective against mucosal infections in the well-established mouse *S. pneumoniae* colonization model. Groups of immunized (PsaA+2'-F-c-di-GMP) or sham-immunized (saline only) mice were intranasally challenged with 4.55×10$^6$ CFU *S. pneumoniae* at day 35 after the first immunization. Mice were sacrificed 3 days after challenge, and the nasopharyngeal tract was lavaged and bacterial numbers in the nasal wash were determined. As seen in FIG. 2 (left panel), results from quantitative bacteriology showed significantly reduced colonization of *S. pneumoniae* in PsaA+2'-F-c-di-GMP immunized mice when compared to sham-immunized mice (P<0.05). Moreover, the magnitude of this reduction was comparable to that attained in mice immunized with PsaA+ CT (Yan H, Kuo Lee R, Tram K, Qiu H, Zhang J, Patel G B, Chen W. *3',5'-Cyclic diguanylic acid elicits mucosal immunity against bacterial infection*. Biochemical and Biophysical Research Communications. 2009; 387(3):581-4). Intranasal immunization of mice with PsaA alone without adjuvant showed no reduction in nasopharyngeal colonization of *S. pneumoniae* as compared to sham-immunized mice as seen in FIG. 2 (right panel). These results indicate that 2'-F-c-di-GMP induces a potent, protective immunity against i.n. challenge with *S. pneumoniae* when co-administered with the PsaA antigen via i.n. route. These data indicate that 2'-F-c-di-GMP is capable of inducing a protective mucosal immunity upon intranasal immunization with specific antigen.

Example 3

Figure 3:
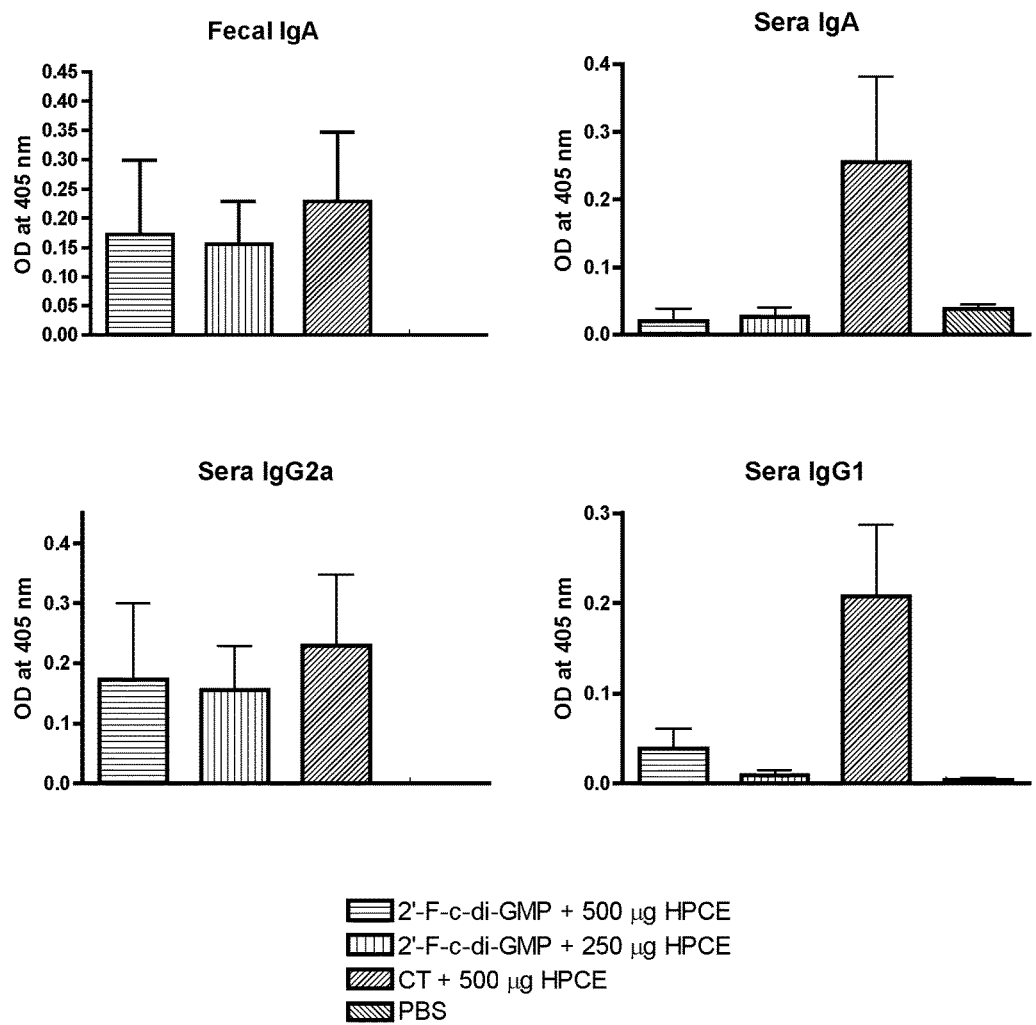
FIG. 3—bar graphs illustrating the effect of oral co-administration of high and low doses of *H. pylori* cell-free sonicate extract (HPCE)+2'-F-c-di-GMP on antigen-specific IgA levels in feces (top left panel) and sera (top right panel) and additionally, IgG1 (bottom right panel) and IgG2a (bottom left panel) levels in serum.

Oral Immunization with 2'-F-cdiGMP-adjuvanted Vaccine Induces Strong Antigen-specific Antibody Responses in the Serum and at Multiple Mucosal Sites To determine if oral administration of 2'-F-c-di-GMP can induce mucosal immune responses to microbial (bacterial and viral) antigens, groups of C57BL/6 mice (n=5) were orally immunized with varying amounts (125-500 µg) of HPCE admixed with 100 µg 2'-F-c-di-GMP, or 500 µg HPCE admixed with 10 µg CT at day 0, 14 and 21. Additional group of mice was sham-immunized with PBS only. The blood and fecal pellets were collected at day 28 and assayed for HPCE-specific IgA, IgG1 and IgG2a by standard ELISA. As it can been seen in FIG. 3, co-administration of both high and low doses of HPCE with 2'-F-c-di-GMP induced substantial amount of antigen-specific IgA levels in feces and serum as well as serum IgG1 and IgG2a levels. The results showed that, compared with sham-immunized mice, 2'-F-c-di-GMP induces substantially higher antigen-specific IgA responses in feces and IgG2a responses in the serum. The responses were similar in the magnitude to those induced by CT, the golden standard of mucosal adjuvant which has undesirable toxicity for human applications. As expected, sham-immunized mice showed no specific antibody responses in the serum or fecal samples as seen FIG. 3. These results demonstrate that 2'-F'-c-di-GMP can enhance mucosal immune responses to microbial antigens when administered via the oral route. These results indicate that 2'-F-c-di-GMP can be used in oral vaccination as a potent mucosal adjuvant.

Example 4

Figure 4:
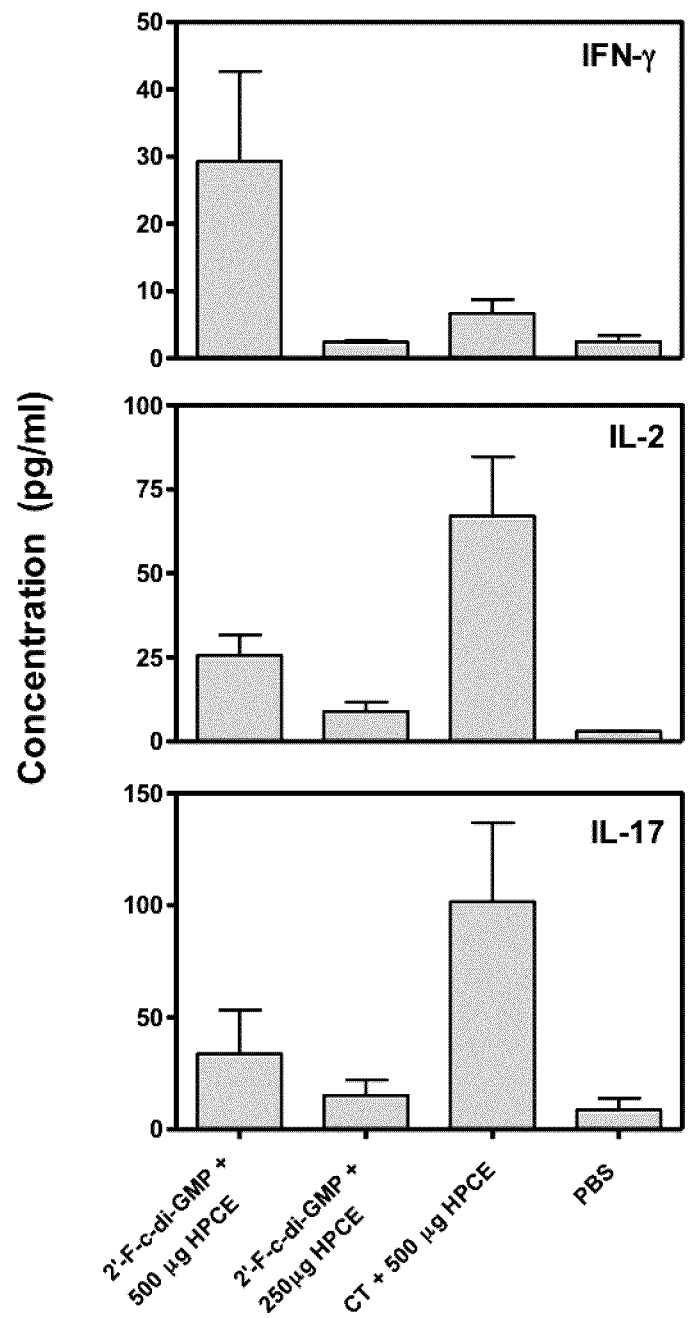
FIG. 4—bar graphs illustrating the effect of oral co-administration of high and low doses of HPCE+2'-F-c-di-GMP on the induction of antigen-specific IFN-γ (top panel), IL-2 (middle panel) and IL-17 (bottom panel) responses in the culture supernatants of splenocytes.

Oral Immunization with 2'-F-c-di-GMP-adjuvanted Vaccine Induces Antigen-specific Th1/Th17 Cytokine Responses To determine if oral administration of 2'-F-c-di-GMP can induce antigen-specific Th1/Th17 cytokine responses to microbial (bacterial and viral) antigens, Groups of 5 C56BL/6 mice were orally immunized with varying amount of *H. pylori* cell free sonicate extract (HPCE) admixed with either 100 µg 2'-F-c-di-GMP or 10 µg cholera toxin (CT, positive control) at day 0, 14 and 21. Additional group of mice were immunized with PBS and served as sham-immunized group. The spleen were collected at day 28 and single cell suspension was prepared for the determination of antigen-specific cytokine responses. The cells were stimulated by 10 µg/ml HPCE and cultured at 37° C. in a 5% $CO_2$ atmosphere for 72 hours. At the end of the culture, the supernatant was collected and assayed for the levels of IFN-γ, IL-2 and IL-17 by Luminex. The production of antigen-specific IFN-γ and IL-17 is associated with the protection against *H. pylori* infection. As it can be seen in FIG. 4, compared to sham-immunized mice, the splenocytes from 2'-F-c-di-GMP immunized mice produced substantially higher amount of IFN-γ, IL-2 and IL-17 in response to HECE stimulation. The amount of IFN-γ produced by the splenocytes from 2'-F c-di-GMP immunized mice was even higher than that produced by the cells from CT-immunized mice although the later mice produced higher amount of IL-2 and IL-17 than the former mice. These results indicate that oral immunization of mice with 2'-F c-di-GMP induces antigen-specific Th1/Th17 cytokine responses which are critical for host defense against mucosal pathogens such as *H. pylori*.

Example 5

Oral Immunization of Mice with 2'-F-c-di-GMP-adjuvanted HPCE Significantly Reduces Gastric Colonization by *H. Pylori*

Figure 5:
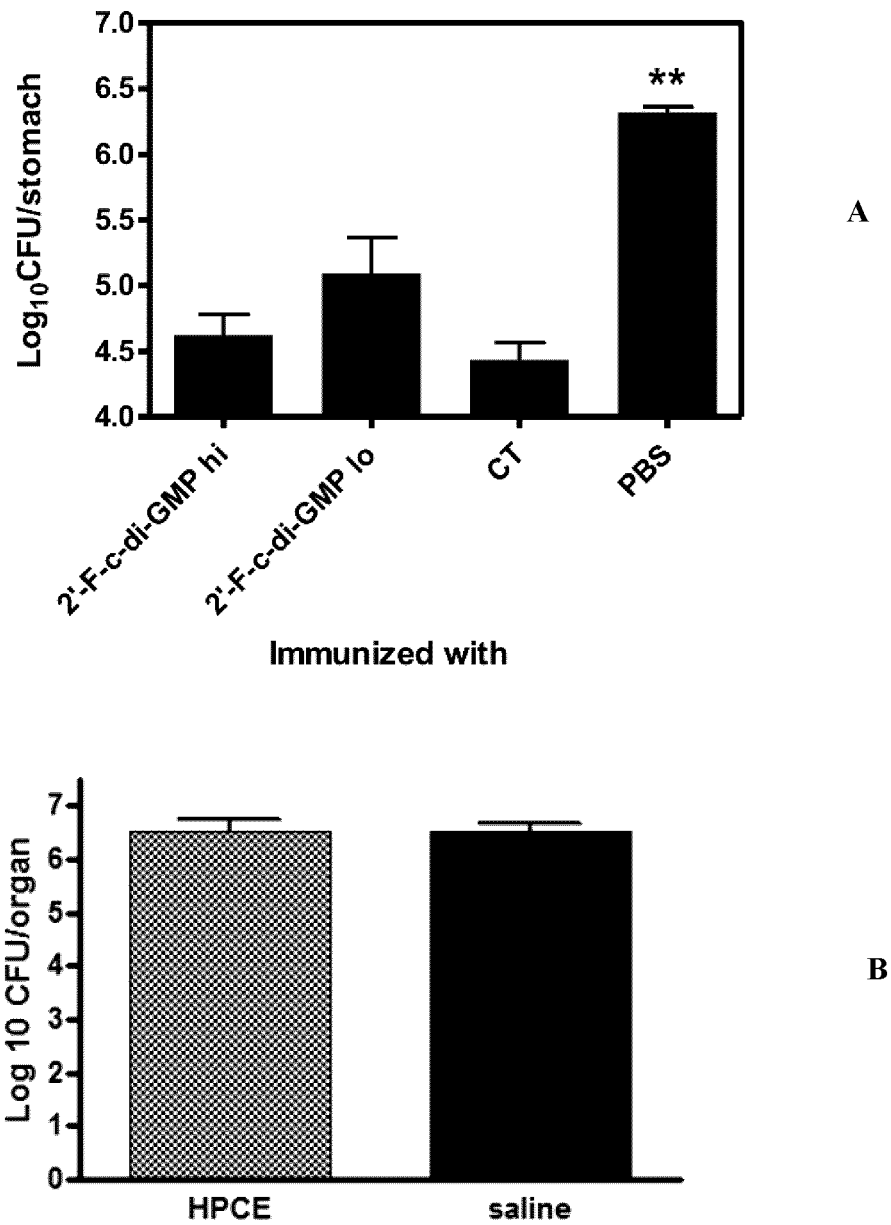
FIG. 5—bar graphs comparing *H. pylori* colonization in HPCE+2'-F-c-di-GMP orally immunized mice and sham-immunized mice (Panel A) and mice immunized with HPCE alone and sham (saline)-immunized mice (Panel B).

Next, it was determined if the mucosal immune responses induced by the 2'-F-c-di-GMP adjuvanted *H. pylori* vaccine are protective against mucosal infections in the well-established mouse model of *H. pylori* (Lee A, O'Rourke J, De Ungria M C, Robertson B, Daskalopoulos G, Dixon M F. *A standardized mouse model of Helicobacter pylori infection.* Gastroenterology 1997; 112: 1386-97). Groups of immunized (HPCE+2'-F-c-di-GMP or HPCE+CT) or sham-immunized (PBS only) mice were orally challenged with $10^8$ CFU *H. pylori* SS1 three times at every second day, starting at day 35 after the first immunization. Mice were sacrificed 6 weeks after the first challenge, and the stomach tissue was collected and processed for the determination of the bacterial burdens. As seen in FIG. 5, results from quantitative bacteriology showed significantly reduced colonization of *H. pylori* in HPCE+2'-F-c-di-GMP immunized mice (Panel A) when compared to sham-immunized mice (P<0.05). The results showed that, compared to sham (PBS)-immunized mice, both low or high doses of HPCE+2'-F-c-di-GMP immunized mice showed significantly reduced bacterial burdens in the gastric mucosa. Moreover, the magnitude of this reduction was comparable to that attained in mice immunized with HPCE adjuvanted with CT, the gold standard of mucosal adjuvant. In addition, immunization of mice with HPCE alone (FIG. 5, Panel B) also failed to reduce the bacterial colonization. These results indicate that 2'-F-c-di-GMP induces a potent protective immunity against gastric infection with *H. pylori* when co-administered with HPCE via oral route. These results indicate that 2'-F-c-di-GMP is capable of inducing a protective mucosal immunity against mucosal pathogens upon oral immunization with specific antigen.

Example 6

Figure 6:
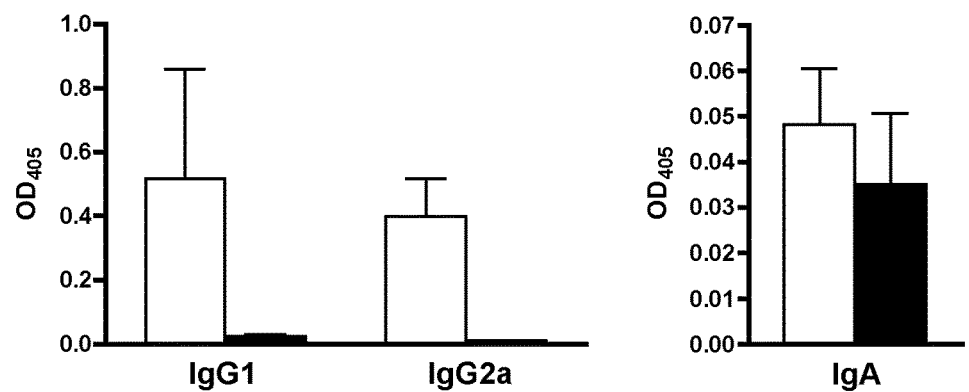
FIG. 6—bar graphs illustrating the effect of oral co-administration of bacterial flagellin antigens+2'-F-c-di-GMP on antigen-specific IgA levels in feces (right panels) and specific IgG1 and IgG2a levels in sera (left panels). Upper panel: *Listeria* flagellin immunization; lower panel: *C. difficile* flagellin immunization. Open bars: flagellin-immunized; Solid bars: sham-immunized.
Figure 6:
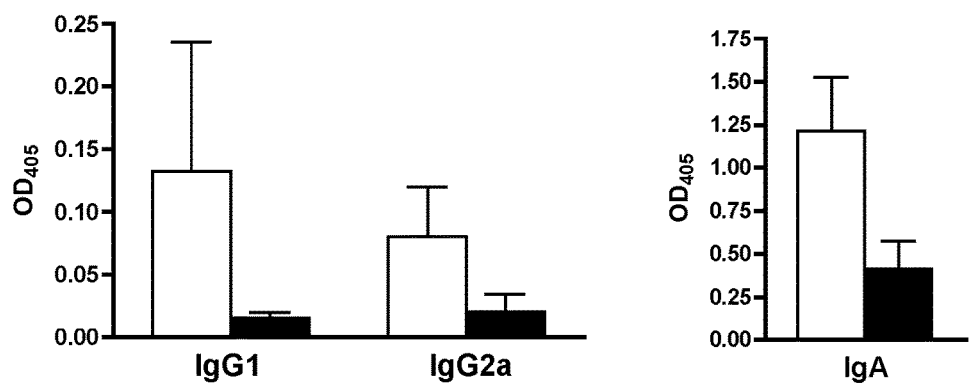

Oral Immunization with 2'-F-cdiGMP-adjuvanted Vaccine Induces Strong Antigen-specific Antibody Responses in the Serum and at Multiple Mucosal Sites As an additional example to demonstrate the capability of oral administration of 2'-F-c-di-GMP can induce mucosal immune responses to microbial (bacterial and viral) antigens, groups of BALB/c mice (n=3) were orally immunized with different amounts of bacterial flagellin antigens purified from *Listeria* (50 µg) or *C. difficile* (30 µg) admixed with 75 µg 2'-F-c-di-GMP at day 0, 14 and 21. Additional group of mice was sham-immunized with PBS only. The blood and fecal pellets were collected at day 35 and assayed for flagellin-specific IgA, IgG1 and IgG2a by standard ELISA. As it can been seen in FIG. 6, co-administration of 2'-F-c-di-GMP with flaggellin antigens induced substantial amount of *C. difficile* flagellin-specific IgA and small amount of *Listeria* flagellin-specific IgA in feces as well as serum IgG1 and IgG2a responses. The results showed that, compared with sham-immunized mice, 2'-F-c-di-GMP induces substantially higher antigen-specific IgA responses in feces and IgG1 and IgG2a responses in the serum. As expected, sham-immunized mice showed no or background levels of specific antibody responses in the serum or fecal samples as seen FIG. 6. These results provide additional examples that 2'-F'-c-di-GMP can enhance mucosal immune responses to microbial antigens when administered via the oral route. These results indicate that 2'-F-c-di-GMP can be used in oral vaccination as a potent mucosal adjuvant.

What is claimed is:

1. A method for enhancing an immune response to an administered vaccine, comprising:
   administering a vaccine with an effective amount of an adjuvant comprising a fluorinated cyclic dinucleotide or a pharmaceutically acceptable salt thereof, wherein the fluorinated cyclic dinucleotide has the following structure:

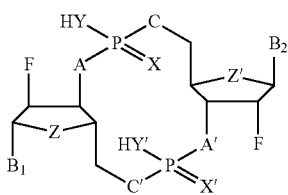

wherein A, C, A' and C' are independently selected from NH, O or S; X, Y, X', and Y' are independently selected from O or S; Z and Z' are independently selected from O, S, NH or CH$_2$; and B$_1$ and B$_2$ are independently a purine selected from:

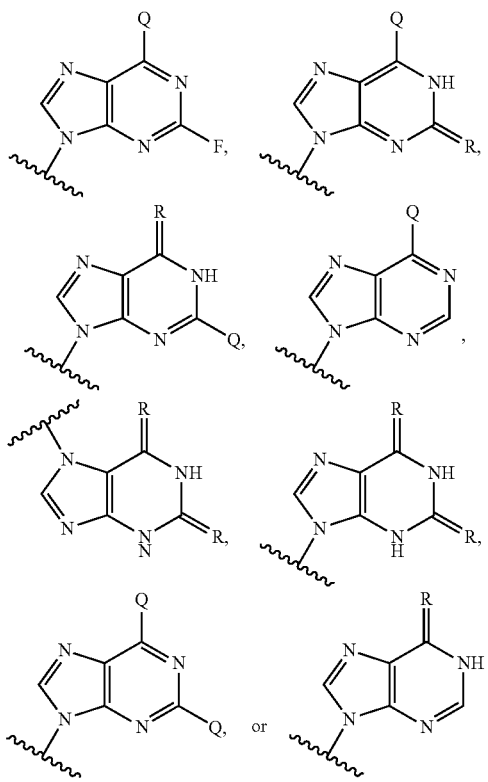

wherein Q is hydrogen or NH$_2$; nitrogen is optionally substituted with C$_1$-C$_6$ alkyl or C$_1$-C$_6$ acyl group; and R is O or S.

2. The method according to claim 1, wherein the fluorinated cyclic dinucleotide is 2'-F-c-di-GMP having the following structure:

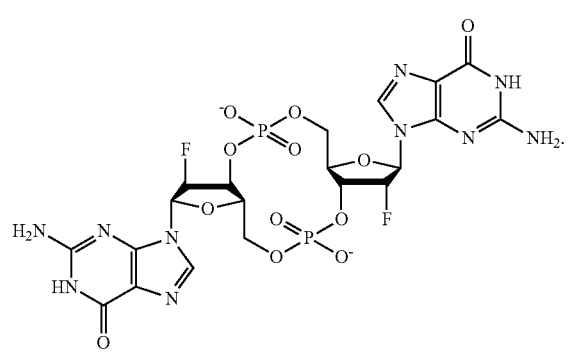

3. The method according to claim 1, wherein said vaccine is an oral vaccine for the prevention or treatment of a *H. pylori* infection, a *C. difficile* infection or a *Listeria* infection.

4. The method according to claim 1, wherein said vaccine and said adjuvant are administered as separate dosage forms.

5. The method according to claim 1, wherein said vaccine and said adjuvant are administered as an admixture.

6. The method according to claim 1, wherein said immune response comprises an antigen-specific mucosal immune response.

7. The method of claim 6, wherein said immune response is characterized by an antigen-specific secretive IgA antibody response at mucosal sites.

8. The method according to claim 1, wherein said immune response further comprises an antigen-specific humoral immune response.

9. The method according to claim 1, wherein said immune response further comprises an antigen-specific cellular immune response.

10. The method according to claim 1, wherein said vaccine is an oral vaccine or an intranasal vaccine.

* * * * *